United States Patent [19]

Gehlbach

[11] Patent Number: 5,131,395
[45] Date of Patent: Jul. 21, 1992

[54] ULTRASONIC APPARATUS FOR GUIDING NEEDLES INTO SURFACE VESSELS

[76] Inventor: Steve M. Gehlbach, 1825 Austin Ave., Los Altos, Calif. 94024

[21] Appl. No.: 526,124

[22] Filed: May 21, 1990

Related U.S. Application Data

[63] Continuation-in-part of Ser. No. 500,710, Mar. 28, 1990.

[51] Int. Cl.$^5$ ............................................. A61B 8/14
[52] U.S. Cl. ............................................. 128/662.05
[58] Field of Search ...................... 128/662.03, 662.04, 128/662.05, 662.06, 661.07

[56] References Cited

U.S. PATENT DOCUMENTS

| | | | |
|---|---|---|---|
| 3,556,709 | 1/1971 | Omizo | 128/662.05 |
| 3,721,227 | 3/1973 | Larson et al. | 128/662.05 |
| 4,582,067 | 4/1986 | Silverstein et al. | 128/661.09 |
| 4,681,103 | 7/1987 | Boner et al. | 606/1 |
| 4,887,606 | 12/1989 | Yock et al. | 128/662.05 |
| 5,000,185 | 3/1991 | Yock | 128/662.03 |
| 5,080,104 | 1/1992 | Marks et al. | 128/662.05 |

Primary Examiner—William E. Kamm
Assistant Examiner—Kevin Pontius
Attorney, Agent, or Firm—Flehr, Hohbach, Test, Albritton & Herbert

[57] ABSTRACT

An ultrasonic transducer apparatus includes an ultrasonic transducer coupled to a backing member, with a cylindrically shaped hole for accepting a hypodermic needle. The transducer transmits ultrasonic sound waves through the skin and toward the vessel of interest. A portion of the energy in the sound waves is reflected by blood cells flowing within an underlying vessel. The reflected energy is "Doppler shifted" in frequency from the transmitted sound waves because the blood cells are moving relative to the position of the transducer, with the shift in frequency being proportional to the velocity of the blood cells flowing in the vessel. The Doppler shifted reflected signal is detected and amplified and then used to drive an audio speaker, thereby generating an audible signal. As the needle is brought closer to a vessel, the Doppler sounds become stronger in amplitude and the angle of the needle with respect to the vessel affects the pitch of the Doppler shifted signal. These audible indications are used by a clinician, while varying the angle of the needle, to identify the proper direction to proceed in order to insert the needle in the vessel.

13 Claims, 3 Drawing Sheets

ULTRASONIC APPARATUS FOR GUIDING NEEDLES INTO SURFACE VESSELS

This application is a continuation-in-part of application Ser. No. 07/500,710, filed Mar. 28, 1990.

The present invention relates generally to hypodermic needles used by medical personnel and particularly to methods and systems for guiding such needles into vessels located near the surface of the body.

BACKGROUND OF THE INVENTION

Physicians frequently insert hollow hypodermic needles into vessels near the surface of the body of a human patient to introduce fluids, draw blood, insert catheters, and perform other diagnostic and therapeutic activities. The present invention provides apparatus for isolating or locating an artery or vein near the surface of the human body and assists the clinician in inserting hypodermic needles at the proper location. The present invention therefore shortens the time required for proper needle insertion, reducing the cost of medical case and minimizing patient discomfort.

This application is related to the subject matter of application Ser. No. 07/500,710, filed Mar. 28, 1990, entitled Ultrasonic Guided Needle, hereby incorporated by reference, which relates to locating a hypodermic needle into arteries or veins deep within tissue. That application describes apparatus which transmits a sonic beam through the hollow metal needle of a standard hypodermic needle. When locating vessels deep with a body using the apparatus described in Ser. No. 07/500,710, the needle typically must be aspirated and located below the skin before the angulating the needle to locate the vessel. Surface vessels cannot be isolated in this manner, since the searching operation must be performed prior to piercing the skin.

SUMMARY OF THE INVENTION

In summary, the present invention uses a transducer assembly having a cylindrical hole through which a hypodermic needle is inserted. The transducer transmits ultrasonic sound waves through the skin and toward the vessel of interest. A portion of the energy in the sound waves is reflected by blood cells flowing within an underlying vessel. The reflected energy is "Doppler shifted" in frequency from the transmitted sound waves because the blood cells are moving relative to the position of the transducer, with the shift in frequency being proportional to the velocity of the blood cells flowing in the vessel. The Doppler shifted reflected signal is detected and amplified and then used to drive an audio speaker, thereby generating an audible signal. As the needle is brought closer to a vessel, the Doppler sounds become stronger in amplitude and the angle of the needle with respect to the vessel affects the pitch of the Doppler shifted signal. These audible indications are used by the clinician, while varying the angle of the needle, to identify the proper direction to proceed in order to insert the needle in the vessel.

BRIEF DESCRIPTION OF THE DRAWINGS

Additional objects and features of the invention will be more readily apparent from the following detailed description and appended claims when taken in conjunction with the drawings, in which:

DESCRIPTION OF THE PREFERRED EMBODIMENT

Figure 1:
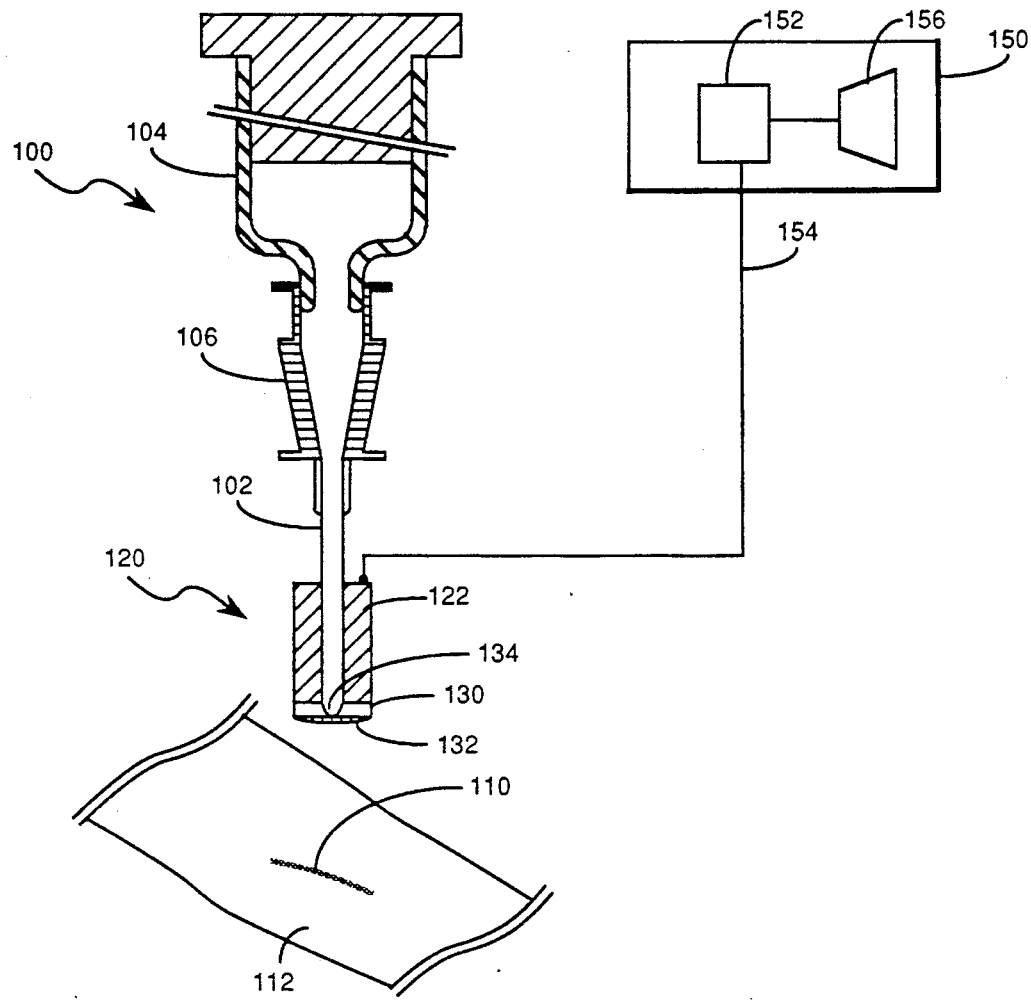
FIG. 1 is a conceptual representation of the present invention.

Referring to FIG. 1, there is shown a needle and syringe apparatus 100, including a hollow steel needle 102 coupled to a syringe 104 by a needle coupling 106, also known as a needle hub. The needle and syringe apparatus 100 may be used to either inject a fluid into or draw blood from an artery, vein, or other vessel, such as vein 110 near the surface of a person's arm 112.

The hypodermic needle 102 is inserted into a transducer assembly 120 that has a center hole 124 of sufficient size to easily accommodate the needle 102. For the purposes of describing this invention, the term "hypodermic needle" is defined to mean any hollow metallic needle used in medical procedures.

Figure 2:
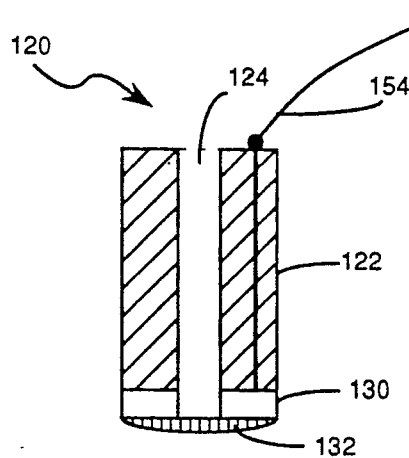
FIG. 2 depicts the transducer apparatus of the present invention as used in the preferred embodiment.

Referring to FIGS. 1 and 2, the transducer assembly includes a cylindrically shaped backing or holding member 122, typically made of plastic, coupled to an ultrasonic transducer 130 which is also cylindrical in shape. The assembly 120 has a center hole 124 which is sized so as to easily accept a standard hypodermic needle of predefined size. The end of the assembly 120 is capped with a membrane 132, which is preferably a sterile, acoustic coupler that facilitates sliding the transducer along the skin of the patient in any direction while trying to locate the best position for inserting the needle 102 into a vessel 110 below the skin.

Figure 3:
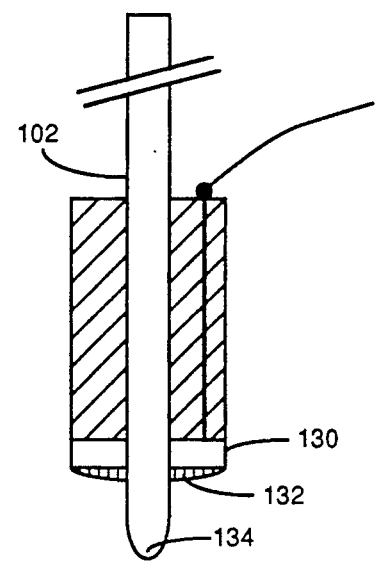
FIG. 3 schematically depicts the transducer apparatus of FIG. 2, with a hypodermic needle extending through its focusing membrane.

The membrane 132 is a thin, frangible, plastic membrane affixed to the distal end of the transducer 130, which prevents the distal end 134 of needle 102 from projecting beyond the transducer 130, which is necessary during the process of searching for and locating the vessel 110. Otherwise the needle 102 would tend to pierce the patient's skin before the vessel is fully isolated or located. In addition, the membrane is preferably concave in shape and is used for assisting in focusing the ultrasonic beam generated by the transducer 130 by virtue of its acoustic velocity differing from that of the surrounding medium (tissue or water), similar to the manner in which light is focused by a lens. After the proper vessel 110 is located, the needle 102 is then advanced to pierce the frangible membrane 132 (as shown in FIG. 3), then the skin and finally the vessel of interest.

The transducer 130 is typically a piezoelectric crystal with a resonant frequency in the ultrasonic frequency range (e.g., 1.0 to 20 megahertz). The crystal transducer 130 is coupled to an electrical subsystem 150 which includes a circuit 152 for generating crystal excitation signals and for amplifying Doppler shifted waves which are reflected back toward the crystal 130.

A portion of the generated ultrasonic sound waves is reflected by the tissues 110 and 112 at which the needle is pointed. Most importantly, if the needle is pointed at a vessel 110 in which blood is flowing, the frequency of the reflected sound waves is Doppler shifted by an amount proportional to the velocity of blood cell flow in the vessel. The reflected sound waves impinge on the piezoelectric crystal 130, thereby creating an a.c. electrical signal on line 154 with a frequency component that matches the frequency of the Doppler shifted sound waves. Note that electrical line 154 is embedded in the backing member 122 and is used to couple the piezoelectric crystal transducer 130 to the electrical subsystem 150.

The electrical circuit 152 detects and amplifies the Doppler shifted signal and the resulting signal is used to drive a speaker 156 and thereby generate an audible signal. As the needle is brought closer to the vessel 110, the Doppler sounds become stronger in amplitude and the angle of the needle 102 with respect to the vessel affects the pitch of the Doppler shifted signal. These audible indications are used by the clinician, while varying the angle of the needle, to identify the proper direction to proceed in order to insert the needle in the vessel.

Needles and syringes are typically sterilized at the point of manufacture, packaged in sterile materials, and used only once. Similarly, it is important for the transducer assembly 120 to be sterile and very inexpensive to manufacture so as to allow it to be disposable after a single use. As shown in FIG. 2, the three components (backing member 122, transducer 130 and membrane 132) of the transducer assembly 120 are all very inexpensive to manufacture and easy to package in a sterile envelope or sleeve such as those used for packaging hypodermic needles and syringes.

Figure 4:
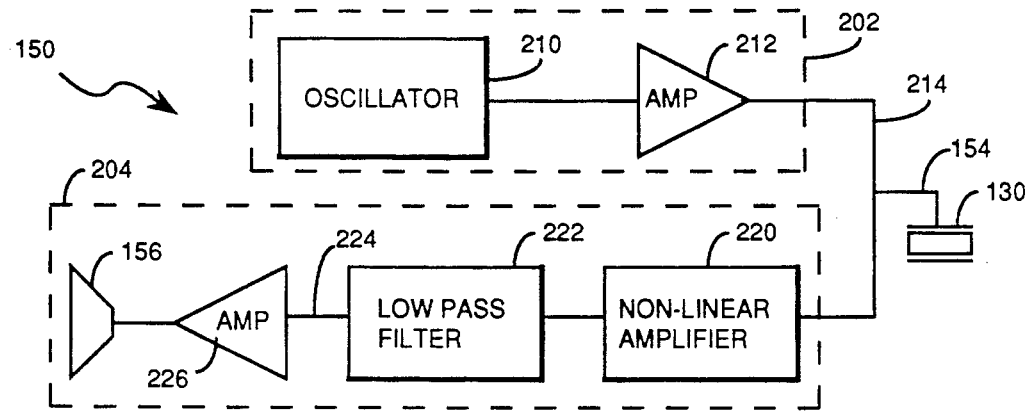
FIG. 4 is a block diagram of a first preferred embodiment of a circuit for generating and processing ultrasonic signals in accordance with the present invention.

Referring to FIG. 4, the circuit 150 includes a high output impedance transmitter 202 and a receiver 204. The transmitter 202 comprises an oscillator 210 which generates a continuous wave a.c. signal with a predefined ultrasonic frequency and a high output impedance amplifier 212. Thus the amplifier 212 outputs a continuous wave (CW) ultrasonic frequency signal on line 214. The signal on line 214 continuously excites the crystal 130 at its resonant frequency. The transmitter 202 (i.e., the amplifier 212) has a high output impedance compared to the crystal 130 so that reflected signals being received by the crystal 130 are not significantly attenuated by the output port of the amplifier 212.

Reflected sound waves impinge on the piezoelectric crystal 130, creating an a.c. electrical signal on line 214 with a frequency component that matches the frequency of the (Doppler shifted) reflected sound waves.

The receiver 204 is capable of detecting very weak Doppler signals in the presence of the very high amplitude transmitting signal on line 214. The first stage of the receiver is a non-linear amplifier 220 that extracts the Doppler shifted reflected signals from the combination of transmitted and received signals on line 214. It does so in the following manner. The signal on line 214 can be written as a combination of transmitted and received energy as follows:

$$S(t) = A(t)\cos(\omega t) + K \cdot B(t)\cos(\omega + \Delta\omega)t \qquad (Eq.1)$$

where $A(t)\cos(\omega t)$ is the transmitted signal, $A(t)$ being the amplitude modulation of the transmitted signal and $\omega$ being the center frequency of the transmitted signal. $K \cdot B(t)\cos(\omega + \Delta\omega)t$ is the Doppler modulated received signal with K being a gain factor much smaller in value than 1.0, $\Delta\omega$ being the Doppler shift in the frequency of the received signal, and $B(t)$ being the amplitude modulation of the received signal—which is a function of the transducer transmission and reception process.

The frequency shift $\Delta\omega$ is related to blood flow by the following equation:

$$\Delta\omega = 2\frac{v}{c}\omega\cos(\phi) \qquad (Eq. 2)$$

where v is the particle flow velocity, c is the speed of sound and $\phi$ is the transducer orientation angle.

In the preferred embodiment, the non-linear amplifier is a half-wave rectifier device that amplifies the positive going excursions of the signal on line 214 and clips the negative excursions. The non-linear amplifier response can be written as follows:

$$P_o(t) = C \cdot (1 + sgn[P_i(t)]) \cdot P_i(t) \qquad (Eq.3)$$

where $P_o(t)$ is the output signal, $P_i(t)$ is the input signal, C is the relative gain of the amplifier, and sgn[x] is a function which is equal to +1 when x is positive and is equal to −1 when x is negative. Since the transmitted signal is much larger (e.g., 80 dB greater) than the reflected Doppler signal, the effect of the amplifier 220 is to mix (i.e., multiply) the Doppler signal with the transmitted signal, which results in shifting the Doppler signal down to the baseband.

The output of the amplifier 220 is therefore low pass filtered by filter 222 to generate a signal S(t) having the form:

$$S(t) = K_1 \cdot A(t) + K_2 \cdot B(t)\cos(\Delta\omega t) \qquad (Eq.4)$$

where S(t) is the low pass filtered signal output on line 224, and $K_1$ and $K_2$ are constants proportional to the gain of the amplifier 220. In most cases A(t) is a non-varying or DC value, and the low pass filtered signal S(t) is primarily equal to the frequency deviation of the Doppler shift in the received or reflected signal.

The low pass filtered signal on line 224 is then amplified by amplifier 226 and presented to an audio speaker 156 for interpretation by a clinician.

As a practical matter, the methods of manufacturing small, high frequency transducers (i.e., crystals 130) do not allow the frequency of resonance to be held to a very precise pre-determined value without significantly increasing the cost of manufacturing those transducers. Typically, when using small ultrasonic crystal transducers, the resonant frequency will be quite high, such as in the range of 10 to 20 Megahertz. Unfortunately, the resonant frequency from crystal to crystal can vary by more than 1 Megahertz, and an excitation signal which differs in frequency from the resonant frequency by 1 Megahertz does not allow the crystal transducer to transmit a strong outgoing ultrasonic signal. Where this is of concern, the circuit shown in FIG. 5 can be used.

Figure 5:
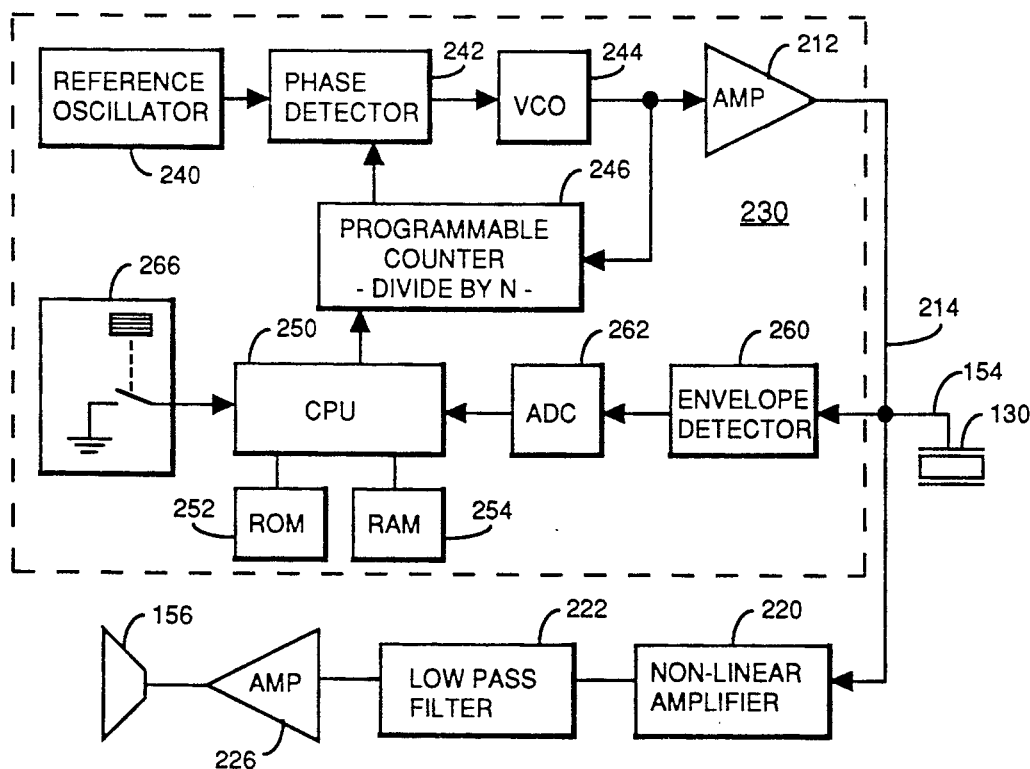
FIG. 5 is a block diagram of a second preferred embodiment of a circuit for generating and processing ultrasonic signals in accordance with the present invention.

The circuit in FIG. 5 is the same as the one in FIG. 4, except that the apparatus used to generate the excitation signal has been modified and is computer controlled. The purpose of the additional circuitry in the transmitter is to find a frequency signal that is close to the resonance frequency of the ultrasonic crystal transducer 130.

In particular, the transmitter circuit 230 in FIG. 5 is essentially a programmable oscillator. A reference oscillator 240 outputs a signal with a fixed frequency, such as 100 Kilohertz. Phase detector 242 detects phase differentials between the signals output by reference oscillator 240 and programmable counter 246 and outputs a voltage signal which corresponds to the error detected. The output signal from the phase detector 242 drives a voltage controlled oscillator (VCO) 244, which outputs an a.c. signal which oscillates at a frequency corresponding to the output voltage from the phase detector 242. In this circuit the VCO 244 outputs ultrasonic frequency signals in the range needed to drive an ultrasonic crystal transducer 130. Programmable counter 246 divides the frequency of the a.c. signal from the VCO 244 by a specified integer N, and sends the resulting lower frequency a.c. signal to phase detector 242.

Thus the phase detector's function is to output a signal proportional to the error between the reference oscillator 240 signal and the VCO output signal after it has been divided by N. The frequency of the reference oscillator 240 signal is equal to the step size between output frequency values that can be generated by varying the value of N.

In this particular circuit, a microprocessor (CPU) 250 (e.g., an 8086 microprocessor made by Intel) specifies the value of N to be used by the programmable counter 246 in accordance with a program stored in read only memory 252. During calibration of the transmitter circuit 230, the CPU 250 monitors the amplitude of the transmitted signal on line 214. At resonance, the crystal 130 has a much lower impedance than at other driving frequencies and the amplitude of the measured signal on line 214 will be much less than at adjacent frequencies. The transmitter 230 is basically a controllable frequency source which monitors the signal on line 214 during calibration so as to identify the resonance frequency.

More particularly, envelope detector 260 is used to detect the amplitude of the signals on line 214. The envelope signal is converted from analog to digital form by an analog to digital converter (ADC) 262 so that the envelope signal can be read by the CPU 250. The amplitude value associated with each of a predefined set of frequencies is stored by the CPU 250 in a random access memory 254 so that the frequency which results in the lowest amplitude signal on line 214 can be identified. Using a reference oscillator 240 with a frequency of 100 Kilohertz ensures that the selected frequency will be no more than 50 Kilohertz from the crystal's resonance frequency—which is sufficient to ensure that a good quality ultrasonic signal is transmitted into the tissue.

Figure 6:
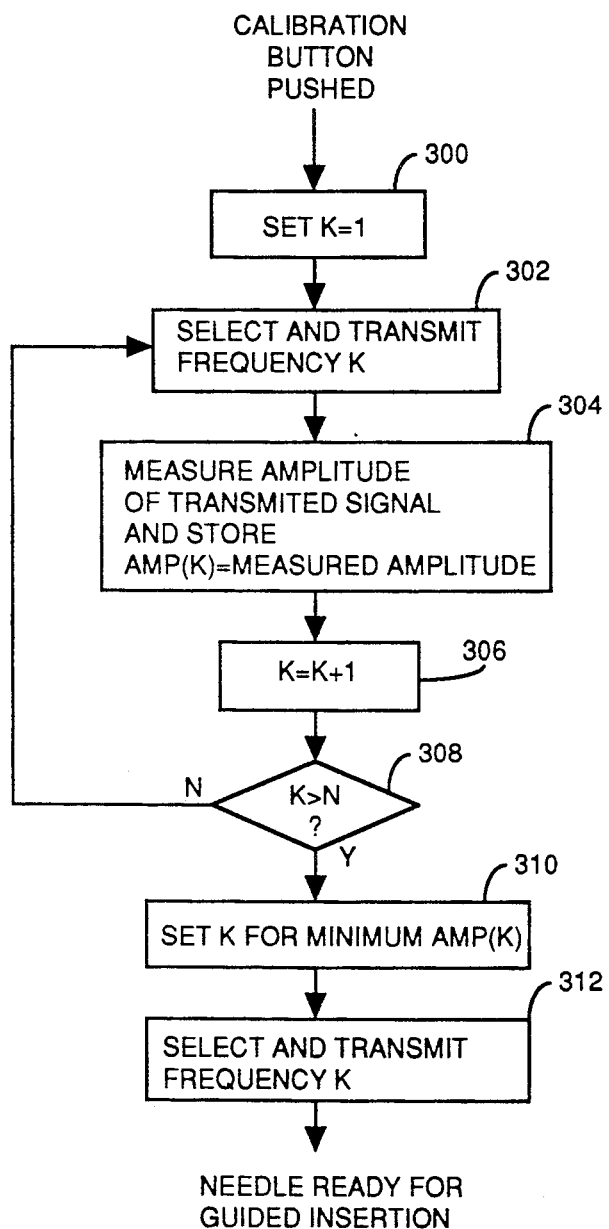
FIG. 6 is a flow chart of the calibration process used by the circuit shown in FIG. 5.

Referring to FIGS. 5 and 6, calibration begins when a clinician presses calibration button 266. This initiates the execution of a calibration routine (stored in ROM 252) by the CPU 250. A flow chart of the calibration routine is shown in FIG. 6.

The basic strategy of the calibration routine is to step through a predefined set of frequencies, such as the frequencies between 10 Megahertz and 20 Megahertz in increments of 100 Kilohertz. See steps 300, 302, 306 and 308 which sequentially transmit each frequency K in a predefined series of frequency values. For each transmitted frequency, the amplitude of the signal on line 214 is read, via envelope detector 260 and ADC 262, by the CPU 259 and stored in RAM 254 (see step 304). After all the frequencies have been read (step 308), the stored amplitude values are searched to find the minimum measured transmit signal on line 214 (step 310). The frequency K associated with that value is selected and the transmitter frequency is set at that value so that the transmitter will from then on transmit the frequency K closest to the crystal's resonance frequency. The process shown in FIG. 6 can be repeated several times, if necessary, to ensure selection of the best transmission frequency. The CPU 250 then exits the calibration program and the transducer assembly 120 is ready for use (i.e., for directing a needle toward a blood carrying vessel).

As will be understood by those skilled in the art, there are a large number of ways for refining the routine shown in FIG. 6 to ensure selection of the best frequency for each particular crystal 130 used.

While the present invention has been described with reference to a few specific embodiments, the description is illustrative of the invention and is not to be construed as limiting the invention. Various modifications may occur to those skilled in the art without departing from the true spirit and scope of the invention as defined by the appended claims.

What is claimed is:

1. Ultrasonic needle guiding apparatus, comprising:
a single ultrasonic transducer which generates continuous ultrasonic sound waves and which converts reflected ultrasonic sound waves which impinge on said ultrasonic transducer into corresponding electrical signals; said ultrasonic transducer having an aperture sized to accept a round hollow needle;
holding means coupled to said ultrasonic transducer for providing mechanical support to said ultrasonic transducer, said holding means having an aperture aligned with an ultrasonic transducer's aperture and sized to accept a round, hollow needle; and
signal processing means coupled to said ultrasonic transducer for receiving said electrical signals corresponding to said reflected ultrasonic waves, filtering said received electrical signals to reject non-Doppler shifted signals therein and amplifying said filtered received electrical signals so as to detect continuous wave Doppler shifted signals therein;
wherein said amplified filtered electrical signals are indicative of whether a needle inserted into said ultrasonic transducer's aperture is accurately pointed at a blood carrying vessel.

2. Ultrasonic needle guiding apparatus comprising:
an ultrasonic transducer which generates ultrasonic sound waves and which converts reflected ultrasonic sound waves which impinge on said ultrasonic transducer into corresponding electrical signals; said ultrasonic transducer having an aperture sized to accept a round hollow needle;
holding means coupled to said ultrasonic transducer for providing mechanical support to said ultrasonic transducer, said holding means having an aperture aligned with said ultrasonic transducer's aperture and sized to accept a round, hollow needle; and
signal processing means coupled to said ultrasonic transducer for receiving said electrical signals corresponding to said reflected ultrasonic waves, detecting Doppler shifted signals in said received electrical signals, if any, and amplifying said Doppler shifted signals;
said ultrasonic transducer having two ends, including one end which is coupled to said holding means and one end which is distal said holding means, said apparatus further including a frangible membrane affixed to the end of said ultrasonic transducer distal said holding means, whereby said frangible membrane prevents a needle inserted in said apparatus from penetrating a patient's skin while said apparatus is used to locate a vessel under the patient's skin.

3. The ultrasonic needle guiding apparatus set forth in claim 1, further including audio speaker means coupled to said signal processing means for generating audio sounds corresponding to said amplified Doppler shifted signals, wherein said audio sounds are indicative of whether a needle inserted in said apparatus is pointed toward a blood carrying vessel.

4. Ultrasonic needle guiding apparatus, comprising:
a single crystal ultrasonic transducer which transmits continuous ultrasonic waves toward a blood carrying vessel inside a patient and receives continuous ultrasonic waves reflected back toward said ultrasonic transducer; wherein said ultrasonic transducer converts said reflected continuous ultrasonic waves into corresponding electrical signals;
holding means coupled to said ultrasonic transducer for providing mechanical support to said ultrasonic transducer, said ultrasonic transducer and said holding means having an aperture through which a round, hollow needle can be inserted; and
signal processing means coupled to said ultrasonic transducer for transmitting a continuous wave excitation signal to said ultrasonic transducer, receiving said electrical signals corresponding to said reflected continuous ultrasonic waves, detecting Doppler shifted waves in said reflected continuous ultrasonic waves and amplifying said Doppler shifted waves.

5. The ultrasonic needle guiding apparatus set forth in claim 4, said signal processing means including high output impedance transmitter means for transmitting an ultrasonic frequency excitation signal to said ultrasonic transducer via an electrical connection between said signal processing means and said ultrasonic transducer, and signal receiving means for detecting signals on said electrical connection corresponding to Doppler shifted ultrasonic waves reflected back to said ultrasonic transducer.

6. The ultrasonic needle guiding apparatus set forth in claim 4, said signal processing means including high output impedance transmitter means for transmitting a continuous wave ultrasonic frequency excitation signal to said ultrasonic transducer via an electrical connection between said signal processing means and said ultrasonic transducer, and signal receiving means for detecting continuous wave Doppler shifted signals on said electrical connection.

7. Ultrasonic needle guiding apparatus, comprising:
a single crystal ultrasonic transducer which transmits ultrasonic waves toward a blood carrying vessel inside a patient and receives ultrasonic waves reflected back toward said ultrasonic transducer; wherein said ultrasonic transducer converts said reflected ultrasonic waves into corresponding electrical signals;
holding means coupled to said ultrasonic transducer for providing mechanical support to said ultrasonic transducer, said ultrasonic transducer and said holding means having an aperture through which a round, hollow needle can be inserted; and
signal processing means coupled to said ultrasonic transducer for transmitting an excitation signal to said ultrasonic transducer receiving said electrical signals corresponding to said reflected ultrasonic waves, detecting Doppler shifted waves in said reflected ultrasonic waves and amplifying said Doppler shifted waves;
said ultrasonic transducer having two ends, including one end which is coupled to said holding means and one end which is distal said holding means, said apparatus further including a frangible membrane affixed to the end of said ultrasonic transducer distal said holding means, whereby said frangible membrane prevents a needle inserted in said apparatus from penetrating a patient's skin while said apparatus is used to locate a vessel under the patient's skin.

8. Ultrasonic needle guiding apparatus, comprising:
a single crystal ultrasonic transducer which transmits ultrasonic waves toward a blood carrying vessel inside a patient and receives ultrasonic waves reflected back toward said ultrasonic transducer; wherein said ultrasonic transducer converts said reflected ultrasonic waves into corresponding electrical signals;
holding means coupled to said ultrasonic transducer for providing mechanical support to said ultrasonic transducer, said ultrasonic transducer and said holding means having an aperture through which a round, hollow needle can be inserted; and
signal processing means coupled to said ultrasonic transducer for transmitting an excitation signal to said ultrasonic transducer receiving said electrical signals corresponding to said reflected ultrasonic waves, detecting Doppler shifted waves in said reflected ultrasonic waves and amplifying said Doppler shifted waves;
said ultrasonic transducer having a resonant frequency, said signal processing means including:
programmable transmitter means for transmitting a multiplicity of ultrasonic frequency excitation signals, each having a distinct ultrasonic frequency; and
frequency selection means, coupled to said ultrasonic transducer and said programmable transmitter means, for determining which of said excitation signals is closest in frequency to said resonant frequency of said ultrasonic transducer, and for then programming said programmable transmitter means to thereafter transmit excitation signals at said closest frequency.

9. A method of guiding a hypodermic needle toward a blood carrying vessel, the steps of the method comprising:
providing a single ultrasonic transducer having an aperture adapted to receive a hypodermic needle;
providing a hypodermic needle having a distal end and inserting said distal end of said hypodermic needle in said aperture of said ultrasonic transducer;
continuously transmitting ultrasonic waves from said single ultrasonic transducer;
pointing said hypodermic needle toward a blood carrying vessel, causing Doppler shifted ultrasonic waves to be reflected back to said ultrasonic transducer;
receiving electrical signals from said single ultrasonic transducer including signals corresponding both to said continuously transmitted ultrasonic waves and to said Doppler shifted ultrasonic waves; and
filtering said received electrical signals to reject non-Doppler shifted signals therein, and then amplifying the filtered received electrical signals so as to generate a signal corresponding to said Doppler shifted ultrasonic waves;

wherein said amplified filtered electrical signals are indicative of whether said needle is accurately pointed at said blood carrying vessel.

10. The method of guiding a hypodermic needle set forth in claim 9, said method including the steps of transmitting an ultrasonic frequency excitation signal to said ultrasonic transducer via an electrical connection, and receiving said electrical signals comprising converted reflected ultrasonic waves via said same electrical connection;

separating Doppler shifted ultrasonic signals received on said electrical connection from said ultrasonic frequency excitation signal and amplifying the resulting separated Doppler shifted ultrasonic signals.

11. The method of guiding a hypodermic needle set forth in claim 10, said method including the steps of transmitting a continuous wave ultrasonic frequency excitation signal to said ultrasonic transducer via an electrical connection; and receiving continuous wave electrical signals on said electrical connection corresponding to said reflected ultrasonic waves, detecting continuous wave Doppler shifted ultrasonic signals therein and amplifying said Doppler shifted ultrasonic signals.

12. A method of guiding a hypodermic needle toward a blood carrying vessel, the steps of the method comprising:

providing an ultrasonic transducer having an aperture adapted to receive a hypodermic needle, and transmitting an ultrasonic frequency excitation signal to said ultrasonic transducer via an electrical connection;

providing a hypodermic needle having a distal end and inserting said distal end of said hypodermic needle in said aperture of said ultrasonic transducer;

pointing said hypodermic needle toward a blood carrying vessel, causing Doppler shifted ultrasonic waves to be reflected back to said ultrasonic transducer;

converting said reflected ultrasonic waves into corresponding electrical signals; and receiving via said electrical connection said electrical signals corresponding to said reflected ultrasonic waves, separating Doppler shifted ultrasonic signals received on said electrical connection from said ultrasonic frequency excitation signal and amplifying the resulting separated Doppler shifted ultrasonic signals;

wherein said separated Doppler shifted ultrasonic signals are indicative of whether said needle is accurately pointed at said blood carrying vessel;

said ultrasonic transducer having a resonant frequency, said method including the steps of transmitting a multiplicity of ultrasonic frequency excitation signals, each having a distinct ultrasonic frequency, to said ultrasonic transducer via said electrical connection; and determining which of said excitation signals is closest in frequency to said resonant frequency of said ultrasonic transducer means, and thereafter transmitting excitation signals at said closest frequency.

13. A method of guiding a hypodermic needle toward a blood carrying vessel, the steps of the method comprising:

providing an ultrasonic transducer having an aperture adapted to receive a hypodermic needle, said ultrasonic transducer having a resonant frequency;

providing a hypodermic needle having a distal end and inserting said distal end of said hypodermic needle in said aperture of said ultrasonic transducer;

pointing said hypodermic needle toward a blood carrying vessel. causing Doppler shifted ultrasonic waves to be reflected back to said ultrasonic transducer;

converting said reflected ultrasonic waves into corresponding electrical signals; and receiving said electrical signals corresponding to said reflected ultrasonic waves, detecting Doppler shifted ultrasonic signals therein and amplifying said Doppler shifted ultrasonic signals;

wherein said Doppler shifted ultrasonic signals are indicative of whether said needle is accurately pointed at said blood carrying vessel;

said method including the steps of transmitting a multiplicity of ultrasonic frequency excitation signals, each having a distinct ultrasonic frequency, to said ultrasonic transducer via an electrical connection; and determining which of said excitation signals is closest in frequency to said resonant frequency of said ultrasonic transducer means, and thereafter transmitting excitation signals at said closest frequency.

* * * * *